United States Patent [19]

Haga et al.

[11] Patent Number: 4,845,093
[45] Date of Patent: Jul. 4, 1989

[54] N-BENZOYL-N'-PYRIDAZINYLOXYPHE-NYL UREA COMPOUNDS, AND ANTITUMOROUS COMPOSITIONS CONTAINING THEM, AND PROCESS FOR THEIR PREPARATION

[75] Inventors: Takahiro Haga, Kusatsu; Nobutoshi Yamada; Hideo Sugi, both of Moriyama; Toru Koyanagi, Kyoto; hiroshi Okada, Kusatsu, all of Japan

[73] Assignee: Ishihara Sangyo Kaisha Ltd., Osaka, Japan

[21] Appl. No.: 111,080

[22] Filed: Oct. 19, 1987

Related U.S. Application Data

[63] Continuation of Ser. No. 753,152, Jul. 9, 1985, abandoned.

[30] Foreign Application Priority Data

Jul. 24, 1984 [JP] Japan .................................. 59-153754

[51] Int. Cl.⁴ .................... C07D 237/14; A61K 31/50
[52] U.S. Cl. ..................................... 514/247; 544/241
[58] Field of Search ......................... 544/241; 514/247

[56] References Cited

U.S. PATENT DOCUMENTS 4,677,181  6/1987  Haga .................................. 514/274

FOREIGN PATENT DOCUMENTS 109721  7/1982  Japan .

Primary Examiner—Mark L. Berch
Attorney, Agent, or Firm—Oblon, Spivak, McClelland, Maier & Neustadt, P.C.

[57] ABSTRACT

An N-benzoyl-N'-pyridazinyloxyphenyl urea compound having the formula:

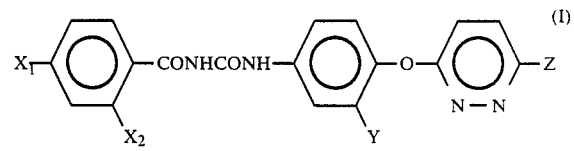

wherein each of $X_1$ and $X_2$ is a hydrogen atom, a halogen atom or a nitro group, Y is a hydrogen atom, a halogen atom or a methyl group which may be substituted by fluorine, and Z is a hydrogen atom, a halogen atom or a trifluoromethyl group, provided that when $X_1$ is a hydrogen atom and $X_2$ is a hydrogen atom or a halogen atom, Y is a methyl group which may be substituted by fluorine and/or Z is a hydrogen atom or a trifluoromethyl group. The compound is useful as an active ingredient for an antitumorous composition.

12 Claims, No Drawings

N-BENZOYL-N'-PYRIDAZINYLOXYPHENYL UREA COMPOUNDS, AND ANTITUMOROUS COMPOSITIONS CONTAINING THEM, AND PROCESS FOR THEIR PREPARATION

This application is a continuation of application Ser. No. 753,152, filed on July 9, 1985, now abandoned.

The present invention relates to novel N-benzoyl-N'-pyridazinyloxyphenyl urea compounds, antitumorous compositions containing them as active ingredients, a method for therapy of cancer by using these compounds, and a process for producing these compounds.

N-benzoyl-N'-pyridazinyloxyphenyl urea compounds are disclosed in Japanese Unexamined Patent Publication No. 15272/1981. It is disclosed that these compounds are useful as pesticides, particularly as insecticides. However, the above publication contains no description of the compounds of the present invention and no indication that the compounds of the present invention have high antitumour activities.

The present inventors have conducted extensive studies on the changes of the substituents for N-benzoyl-N'-pyridazinyloxyphenyl urea compounds, and have finally found that novel N-benzoyl-N'pyridazinyloxyphenyl urea compounds having certain specific substituents have high antitumour activities. The compounds of this type are generally hardly soluble in both water and organic solvents, and accordingly poorly absorbable by the gut. Therefore, depending upon the manner of administration, they sometimes hardly exhibit antitumour activities, and there is a limitation for the intraperitoneal administration of such drugs for curing purposes. Whereas, it has been found that the compounds of the present invention are practically useful for the treatment of tumour or cancer and exhibit excellent antitumour activities by a simple manner of administration and in a simple formulation for the administration without bringing about side effects. The present invention is based on these discoveries.

Namely, the present invention provides an N-benzoyl-N'-pyridazinyloxyphenyl urea compound having the formula:

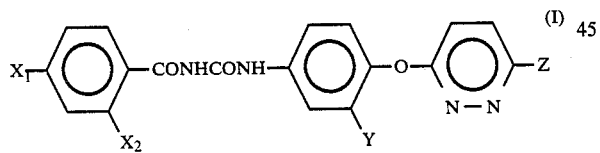

wherein each of $X_1$ and $X_2$ is a hydrogen atom, a halogen atom or a nitro group, Y is a hydrogen atom, a halogen atom or a methyl group which may be substituted by fluorine, and Z is a hydrogen atom, a halogen atom or a trifluoromethyl group, provided that when $X_1$ is a hydrogen atom and $X_2$ is a hydrogen atom or a halogen atom, Y is a methyl group which may be substituted by fluorine and/or Z is a hydrogen atom or a trifluoromethyl group.

The present invention also provides an antitumorous composition containing such a compound as the active ingredient, a method for therapy of cancer by using such a compound, and a process for producing such a compound.

Now, the present invention will be described in detail with reference to the preferred embodiments.

In the above-mentioned formula I, $X_1$ is preferably a hydrogen atom, $X_2$ is preferably a nitro group, Y is preferably a halogen atom or a methyl group which may be substituted by fluorine and Z is preferably a halogen atom. Particularly preferred is a case where Y is a methyl group which may be substituted by fluorine, especially a methyl group or a trifluoromethyl group.

As the halogen atom for $X_1$, $X_2$, Y and Z in the formula I, there may be mentioned a fluorine atom, a chlorine atom, a bromine atom or an iodine atom. As the methyl group which may be substituted by fluorine, for Y in the formula I, there may be mentioned a methyl group, a monofluoromethyl group, a difluoromethyl group or a trifluoromethyl group.

The N-benzoyl-N'-pyridazinyloxyphenyl urea compound of the above-mentioned formula I, may be prepared, for instance, as follows:

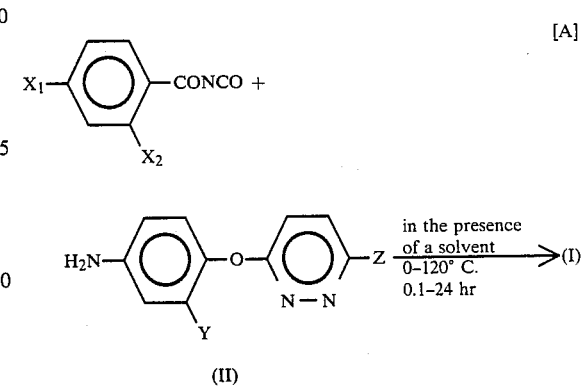

In the above formula, $X_1$, $X_2$, Y and Z are as defined above.

As the solvent to be used in the above reaction, there may be mentioned benzene, toluene, xylene, monochlorobenzene, pyridine, dioxane, tetrahydrofuran, dimethylsulfoxide, dimethyl acetamide, ethyl acetate, acetone, methyl ethyl ketone, etc.

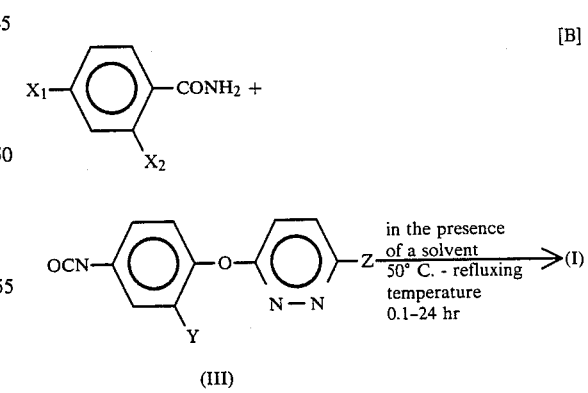

In the formula, $X_1$, $X_2$, Y and Z are as defined above.

As the solvent to be used for the above reaction, there may be mentioned the same solvents as mentioned above for the reaction.

The aniline compound of the formula II used as the tarting material in the above reaction may be prepared, for instance, as follows:

[A-1]

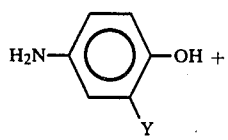

+

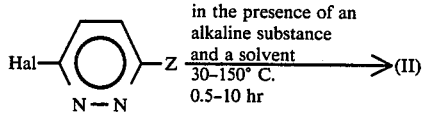

wherein Hal is a halogen atom, and Y and Z are as defined above.

As the alkaline substance to be used, there may be mentioned sodium hydroxide, potassium hydroxide, sodium carbonate, potassium carbonate, sodium hydride, n-butyl lithium, etc. As the solvent, there may be mentioned an aprotic polar solvent such as dimethylsulfoxide, dimethylformamide or hexamethylphosphoramide, a ketone such as acetone, methyl ethyl ketone or methyl isobutyl ketone, etc. This condensation reaction is preferably conducted in the atmosphere of nitrogen gas.

[A-2]

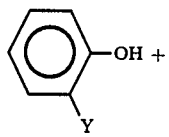

+

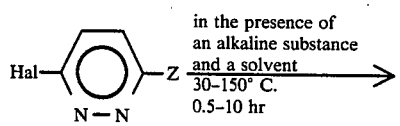

wherein Hal is a halogen atom, and Y and Z are as defined above.

The alkaline substance and the solvent to be used are the same as those used in the above.

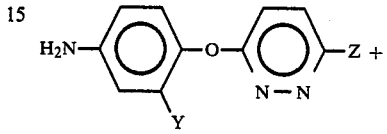

(IV)

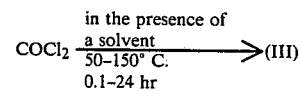

(V)

wherein Y and Z are as defined above.

Further, the isocyanate compound of the formula III used as the starting material in the above reaction, may be prepared, for instance, as follows:

(II)

wherein Y and Z are as defined above.

As the solvent to be used, there may be mentioned a solvent inert to phosgene, such as benzene, toluene, xylene, monochlorobenzene, dioxane, tetrahydrofuran, dimethyl sulfoxide, dimethyl acetamide, ethyl acetate, acetone, methyl ethyl ketone, etc.

Now, specific examples for the synthesis of the compounds of the present invention will be described. Synthetic Example 1:

Synthesis of
N-(2-nitrobenzoyl)-N'-[4-(6-bromo-3-pyridazinyloxy)
-3-chlorophenyl]urea (Compound No. 1) (1) 20 ml of a
dimethylsulfoxide solution containing 3.00 g of
3,6-dibromopyridazine, 3.48 g of anhydrous potassium
carbonate, and 1.81 g of 4-amino-2-chlorophenol, was
reacted in the atmosphere of nitrogen gas at 150° C. for
1.5 hours under stirring. After the completion of the
reaction, the reaction product was poured into water,
and extracted with ethyl acetate. The extract layer was
washed with a 10% sodium hydroxide aqueous solution
and further with water a few times and dried over
anhydrous sodium sulfate. After the treatment with
active carbon, ethyl acetate was distilled off, whereby
2.00 g of 4-(6-bromo-3-pyridazinyloxy)-3-chloroaniline
having a melting point of from 126 to 127° C. was
obtained.

(2) 0.70 g of the aniline compound obtained in the above step (1), was dissolved in 5 ml of dioxane. While stirring the solution, 0.40 g of 2-nitrobenzoylisocyanate dissolved in 5 ml of dioxane, was gradually dropwise added, and the mixture was reacted at room temperature for 17 hours. After the completion of the reaction, the reaction product was poured into hot water, and the obtained precipitates were separated by filtration. To the precipitates, a proper amount of ethyl acetate was added, followed by stirring and filtration to obtain 0.20 g of the desired product having a melting point of from 233 to 235° C.

Synthetic Example 2:

Synthesis of N-(2-nitrobenzoyl)-N'-[4-(6-chloro-3-pyridazinyloxy)-3-methylphenyl]urea (Compound No. 13)

(1) 15 ml of a dimethylsulfoxide solution containing 3.63 g of 3,6-dichloropyridazine, 2.24 g of anhydrous potassium carbonate and 1.00 g of 4-amino-2-methylphenol, was reacted in the atmosphere of nitrogen gas at 90° C. for 1 hour under stirring. After the completion of the reaction, the reaction product was poured into water, and extracted with diethyl ether. The extract layer was washed with water, and then dried over anhydrous sodium sulfate. The solvent was distilled off, and the residue was purified by silica gel column chromatography, whereby 1.59 g of 4-(6-chloro-3-pyridazinyloxy)-3-methylaniline having a refractive index of 1.6052 (26.8° C.) was obtained.

(2) 1.00 g of the aniline compound obtained in the above step (1), was dissolved in 15 ml of dioxane. The solution was dropowise added to 1.22 g of 2-nitrobenzoyl isocyanate, and the mixture was reacted at room temperature for 16 hours. After the completion of the reaction, the product was poured into warm water of 50° C., and the obtained precipitates were separated by filtration, washed with warm water and then dissolved in dimethylsulfoxide. By an addition of methyl alcohol, crystals were precipitated, and separated by filtration, to obtain 1.30 g of the desired product having a melting point of from 233° to 234° C.

Synthetic Example 3:

Synthesis of N-(2-nitrobenzoyl)-N'-[4-(6-chloro-3-pyridazinyloxy)-3-trifluoromethylphenyl]urea (Compound No. 8)

(1) 80 ml of a dimethylsulfoxide solution containing 3.50 g of 3,6-dichloropyridazine, 6.44 g of 2-trifluoromethylphenol and 3.58 g of potassium carbonate, was reacted at 100° C. for 2.5 hours under stirring. After the completion of the reaction, the product was poured into water, and extracted with ethyl acetate. The extract layer was dried over anhydrous sodium sulfate, and then ethyl acetate was distilled off. The residue was purified by silica gel column chromatography, whereby 5.96 g of 3-chloro-6-(2-trifluoromethylphenoxy) pyridazine was obtained.

(2) 5.96 g of the pyridazine compound obtained in the above step (1), was dissolved in 30 ml of concentrated sulfuric acid. To this solution, a mixed solution of 1.65 ml of 60% nitric acid and 3 ml of concentrated sulfuric acid was dropwise added at a temperature of from 20° to 40° C. After the completion of the dropwise addition, the mixture was reacted at room temperature for 10 minutes under stirring. After the completion of the reaction, the reaction product was poured into ice water, and extracted with ethyl acetate. The extract layer was washed with a saturated sodium chloride aqueous solution, and dried over anhydrous sodium sulfate, and then ethyl acetate was distilled off, whereby 5.80 g of 3-chloro-6-(4-nitro-2-trifluoromethylphenoxy)pyridazine having a melting point of from 132° to 133° C. was obtained.

(3) 3.2 g of the pyridazine compound obtained in the above step (2) was dissolved in 30 ml of glacial acetic acid, and the solution was heated to 100° C. Then, 2.8 g of reduced iron was gradually added thereto, and after refluxing the mixture for 5 minutes, the mixture was cooled to room temperature, and after an addition of 50 ml of acetone, was filtered. After distilling off acetone from the filtrate, the residue was poured into water, and extracted with ethyl acetate. The extract layer was washed with water 3 times, dried over anhydrous sodium sulfate, and then purified by silica gel column chromatography, whereby 1.45 g of 4-(6-chloro-3-pyridazinyloxy) -3-trifluoromethylaniline having a melting point of from 111° to 112° C. was obtained.

(4) 1.2 g of the aniline compound obtained in the above step (3), was dissolved in 10 ml of dioxane. Then, 1.10 g of 2-nitrobenzoyl isocyanate dissolved in 10 ml of dioxane was gradually dropwise added to the solution under stirring, and the mixture was reacted at room temperature for 17 hours. After the completion of the reaction, the product was poured into hot water, and the obtained precipitates were separated by filtration. To the precipitates, a proper amount of ethyl acetate was added, followed by stirring and filtration, to obtain 1.7 g of the desired product having a melting point of from 212° to 215° C.

Synthetic Example 4:

Synthesis of N-(2,4-dinitrobenzoyl)-N'-[4-(6-bromo-3-pyridazinyloxy) -3-chlorophenyl]urea (Compound No. 11)

1.10 g of 4-(6-bromo-3-pyridazinyloxy)-3-chloroaniline obtained in the same manner as in the above Synthetic Example 1 (1), was dissolved in 7 ml of dioxane. To this solution, 8 ml of a dioxane solution containing 0.87 g of 2,4-dinitrobenzoyl isocyanate was dropwise added, and the mixture was reacted at room temperature for 4 hours. After the completion of the reaction, the reaction product was poured into warm water, and the precipitates were separated by filtration. The precipitates were stirred in ethyl acetate, and again filtered to obtain 0.80 g of the desired product having a melting point of from 217° to 219° C.

The representative compounds of the present invention are listed below.

Compound No. 1

N-(2-nitrobenzoyl)-N'-[4-(6-bromo-3-pyridazinyloxy)3-chlorophenyl]urea
m.p. 233°–235° C.

Compound No. 2

N-(2-nitrobenzoyl)-N'-[3-chloro-4-(6-chloro-3pyridazinyloxy)phenyl]urea
m.p. 240°–242° C.

Compound No. 3
N-(2-nitrobenzoyl)-N'-[3-chloro-4-(6-iodo-3-pyridazinyloxy) phenyl]urea
m.p. 235°–237° C.

Compound No. 4

N-(2-nitrobenzoyl)-N'-[3-chloro-4-(3-pyridazinyloxy) phenyl]urea
m.p. 210°–211° C.

Compound No. 5

N-(2-nitrobenzoyl)-N'-[3-chloro-4-(6-trifluoro-methyl -3-pyridazinyloxy)phenyl]urea
m.p. 226°–230° C.

Compound No. 6

N-(2-nitrobenzoyl)-N'-[3-bromo-4-(6-bromo-3-pyridazinyloxy)phenyl]urea
m.p. 241°–243° C.

Compound No. 7

N-(2-nitrobenzoyl)-N'-[4-(6-bromo-3-pyridazinyloxy)phenyl]urea
m.p. 219°–222° C.

Compound No. 8

N-(2-nitrobenzoyl)-N'-[4-(6-chloro-3-pyridazinyloxy)-3-trifluoromethylphenyl]urea
m.p. 212°–215° C.

Compound No. 9

N-(2-nitrobenzoyl)-N'-[4-(6-bromo-3-pyridazinyloxy)-3-fluorophenyl]urea
m.p. 221°–224° C.

Compound No. 10

N-(4-chloro-2-nitrobenzoyl)-N'-[4-(6-bromo-3-pyridazinyloxy)-3-chlorophenyl]urea
m.p. 229°–232° C.

Compound No. 11

N-(2,4-dinitrobenzoyl)-N'-[4-(6-bromo-3-pyridazinyloxy)-3-chlorophenyl]urea
m.p. 217°–219° C.

Compound No. 12

N-(2-chlorobenzoyl)-N'-[4-(6-chloro-3-pyridazinyloxy)-3-trifluoromethylphenyl]urea
m.p. 230°–233° C.

Compound No. 13

N-(2-nitrobenzoyl)-N'-[4-(6-chloro-3-pyridazinyloxy)-3-methylphenyl]urea
m.p. 233°–234° C.

Compound No. 14

N-(2,4-dinitrobenzoyl)-N'-[4-(6-chloro-3-pyridazinyloxy)-3-trifluoromethylphenyl]urea
White crystals Among the aniline compounds and the isocyanate compounds represented by the above formulas II and III, those represented by the following formula VI are believed to be novel compounds.

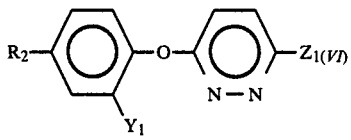

wherein $R_2$ is an isocyanate group or an amino group, $Y_1$ is a methyl group which may be substituted by fluorine, and $Z_1$ is a halogen atom.

In the formula VI, $R_2$ is preferably an amino group, and $Y_1$ is preferably a methyl group or a trifluoromethyl group. Particularly preferred is the one wherein $R_2$ is an amino group, and $Y_1$ is a trifluoromethyl group.

The intermediate compound of the formula VI can be converted to the N-benzoyl-N'-pyridazinyloxyphenyl urea compound of the formula I, which is useful with high antitumour activities.

Now, the antitumour activities, acute toxicity, doses and administration routes of the N-benzoyl-N'-pyridazinyloxyphenyl urea compounds of the present invention will be described.

(1) Antitumour activities

Test Example 1 (Intraperitoneal-intraperitoneal)

To $BDF_1$ mice, p-388 leukemia cells were intraperitoneally inoculated in an amount of $1 \times 10^6$ cells/mouse. A test drug was intraperitoneally administered twice, i.e. one day and four days after the inoculation. The mice were observed for 30 days for survival or death. The increase life span ILS (%)* was obtained with the number of survival days of mice of the control group to which a physiological saline was administered, being evaluated as 100. The results are shown in Table 1. The drugs were dispersions obtained by adding small amounts of surfactants (e.g. Tween-80) to the test compounds.

TABLE 1

| Compound No. | Dose (Active ingredient mg/kg/day) | ILS (%)* |
|---|---|---|
| 1 | 200 | 178 |
| 2 | 200 | 71 |
| 3 | 100 | 92 |
| 4 | 200 | 70 |
| 5 | 200 | 75 |
| 7 | 100 | >120 |
| 8 | 100 | 75 |
| 9 | 100 | 90 |
| 10 | 100 | 111 |
| 11 | 100 | 102 |
| Control | — | 0 |
| 5-Fluorouracil | 60 | 85 |
| Comparative Compound No. 1** | 400 | 42 |
| | 200 | 24 |
| Comparative Compound No. 2*** | 400 | 5 |
| | 200 | −3 |

Notes:
*ILS(%): Increase Life Span, calculated in accordance with the following formula: ILS(%) = MST − 100, where MST is the ratio of median survival time of test and control animals.
**Comparative Compound No. 1: N—(2-chlorobenzoyl)-N'—[3-chloro-4-(3-chloro-6-pyridazinyloxy)phenyl]urea, disclosed in Japanese Unexamined Patent Publication No. 15272/1981.
***Comparative Compound No. 2: N—(2,6-dichlorobenzoyl)-N'—[3-chloro-4-(3-chloro-6-pyridazinyloxy)phenyl]urea, disclosed in the same publication.

Test Example 2 (intraperitoneal-oral)

To $BDF_1$ mice, p-388 leukemia cells were intraperitoneally inoculated in an amount of $1 \times 10^6$ cells/mouse. A test drug was orally administered twice i.e. one day and four days after the inoculation. The mice were observed for 30 days for survival or death, and the ILS (%) of each treated group was obtained with the number of survival days of mice of the control group to which a physiological saline was administered, being evaluated as 0. The results are shown in Table 2. The test drugs and comparative drugs were formulated in accordance with Formulation Example 4 given hereinafter.

TABLE 2

| Compound No. | Dose (Active ingredient mg/kg/day) | ILS (%)* |
|---|---|---|
| 1 | 200 | 58 |
| 9 | 200 | 52 |
| 10 | 400 | 32 |
| Control | — | 0 |
| Comparative Compound No. 1** | 800 | 10 |
| Comparative Compound No. 2*** | 800 | 0 |

Notes:
*ILS(%), Comparative Compound No. 1 and *Comparative Compound No. 2 are the same as mentioned above in the notes of Table 1.

As in evident from the comparative data in Test Example 2, the compounds of the present invention have remarkably high antitumour activities as compared with the comparative compounds. The reason is not clearly understood, but it is assumed that due to the differences in the absorption of the drugs by the gut, the drug concentrations in blood and the transfer property of the drugs to the target portions, there may be substantial difference in the arrival of the drugs to the diseased portions, whereby a substantial difference in the antitumour activities is brought about.

(2) Acute toxicity:

To ddY mice (10 animals), a drug containing one of Compound Nos. 1-7 and 9-13 of the present invention formulated in accordance with Formulation Example 4 was intraperitoneally administered, and the LD50 value was measured and found to be at least 100 mg/kg in each case, and at least 50 mg/kg in the case of Compound Nos. 8 and 14 of the present invention.

(3) Doses and administration routes

As to administration routes in the case of animals, the compounds of this invention are administer as injections such as intraperitoneal injection, intravenous injection, local injection and the like, or as oral drugs. In the case of human beings, said compounds are administer as injections such as intravascular (intravenous or intraarterial) injection, local injection and the like, or oral drugs, suppositories or the like. As to the dose, said compounds are administer continuously or intermittently in a range in which the total dose does not exceed a certain level, in consideration of the results of animal experiments and various conditions. However, the dose may, of course, be properly varied depending on the administration route and on the conditions of a patient or an animal to be treated (for example, age, body weight, sex, sensitivity, food and the like), interval of administration, drugs used in combination with said compounds and the degree of disease. An optimum dose and the number of administrations under certain conditions should be determined by medical specialists.

The antitumorous composition of this invention are prepared in the same manner as for conventional drugs. For example, they are prepared from an active ingredient and various pharmacologically acceptable adjuvants such as inactive diluent and the like. Oral and intravenous administration of these antitumorous compositions is most suitable. The content of the active ingredient in the antitumorous compositions of this invention may vary depending on various conditions and cannot be determined uniquely. It is sufficient that the active ingredient is contained similarly to the case of conventional antitumorous compositions.

The compounds of the present invention are hardly soluble in both water and organic solvents. Therefore, they are preferably formulated into an aqueous suspension which may further contain phospholipids. As a method for producing an aqueous suspension containing no phospholipids, there may be mentioned a method wherein, if necessary, the active compound is preliminarily pulverized into fine powder, then the fine powder of the active compound is added to an aqueous solution containing a surfactant and, if necessary, a defoaming agent, the mixture is pulverized in a wet system until 80% of particles have a particle size of not higher than 5 μm, more preferably not higher than 2 μm, and a thickener is added thereto. As specific examples of the surfactant, there may be mentioned a non-ionic phosphoric acid ester, a polyoxyethylene hardened castor oil, a polyoxyethylene sorbitan fatty acid ester, a sugar ester, a polyoxyethylene polyoxypropylene block polymer, etc. As specific examples of the defoaming agent, there may be mentioned dimethylpolysiloxane, methylphenylsiloxane, a sorbitan fatty acid ester, a polyoxyethylene-polyoxypropylene cetyl ether, silicone, etc. As specific examples of the thickener, there may be mentioned guar gum, alginic acid, gum arabic, pectin, starch, xanthane gum, gelatin, etc. On the other hand, as a method for preparing an aqueous suspension containing a phospholipid, there may be mentioned a method wherein a phospholipid such as soybean phospholipid or yolk phospholipid is used instead of the surfactant in the above-mentioned method, and an antioxidant such as α-tocopherol is used instead of the thickener.

Further, these compounds may be formulated into tablets, capsules, enteric agents, granules, powders, injection solutions or suppositories by common methods for formulations.

Now, Formulation Examples of the antitumour drugs of the present invention will be described.

Formulation Example 1

70 mg of a non-crystalline powder of the above Compound No. 8 was thoroughly mixed with 30 mg of lactose, and 100 mg of the mixture was filled into a capsule to obtain a capsule drug for oral administration.

Formulation Example 2

85 parts by weight of a non-crystalline powder of the above Compound No. 2 was uniformly mixed with 1 part by weight of glucose, 10 parts by weight of corn starch and 1.5 parts by weight of a 5% starch paste, and the mixture was granulated by a wet method. Then, 1 part by weight of magnesium stearate was added thereto. The mixture was tableted to obtain tablets for oral administration.

Formulation Example 3

5 g of the above Compound No. 9 was dissolved in 5 ml of dimethylacetamide, and 25 ml of coconut oil, 7 g of Pegnol HC-17 (manufactured by Toho Kagaku K.K.) and 6 g of HO-10M (manufactured by Toho Kagaku K.K.) were added to obtain an emulsion. To this emulsion, the same amount of sterilized distilled water was added, and the mixture was subjected to ultrasonic treatment for from 20 to 30 seconds to obtain an oily suspension.

Formulation Example 4

The Compound No. 1 of the present invention was preliminarily pulverized by a centrifugal pulverizer. On the other hand, 5 parts by weight of polyoxyethylene (60) hardened castor oil, 0.2 part by weight of silicone and 0.3 part by weight of a polyoxyethylene-polyoxypropylene block polymer were added to 79.5 parts by weight of a physiological saline to obtain an aqueous solution, to which 10 parts by weight of the above pulverized Compound No. 1 of the present invention was added. The mixture was pulverized in a wet system by a sand mill using glass beads (80% of particles having a particle size of not larger than 2 μm). Then, 5 parts by weight of xanthane gum (2% solution) was added thereto to obtain an aqueous suspension.

Formulation Example 5

To an aqueous solution obtained by dissolving 1.5 parts by weight of oxyethylated polyallylphenol phosphate and 0.2 part by weight of silicone in 53.3 parts by weight of a physiological saline, 40 parts by weight of the Compound No. 2 of the present invention was added, and the mixture was pulverized in a wet system in the sand mill by using glass beads (90% of particles having a particle size of not larger than 2 μm). Then, 5 parts by weight of xanthane gum (2% solution) was added thereto to obtain an aqueous suspension.

Formulation Example 6

The Compound No. 1 of the present invention was preliminarily pulverized by a centrifugal pulverizer. 5 parts by weight of the pulverized Compound No. 1 of the present invention was added to an aqueous solution obtained by stirring and dispersing 2 parts by weight of yolk phospholipid, 0.001 part by weight of α-tocopherol and 92.999 parts by weight of a physiological saline. Then, the mixture was pulverized in a wet system in a sand mill by using glass beads (80% of particles having particle size of not larger than 2 μm) to obtain an aqueous suspension.

I claim:

1. An N-benzoyl-N'-pyridazinyloxyphenyl urea compound having the formula:

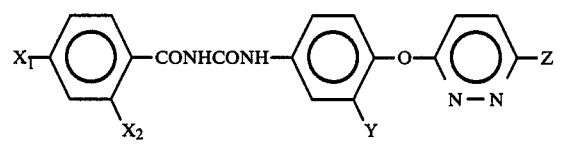

wherein $X_1$ is a hydrogen atom, a halogen atom or a nitro group, $X_2$ is a nitro group, Y is a hydrogen atom, a halogen atom or a methyl group which is unsubstituted or is substituted by fluorine, and Z is a fluorine, chlorine or bromine atom.

2. A composition for treating p-388 leukemia in a mouse, comprising an N-benzoyl-N'-pyridazinyloxyphenyl urea compound as defined in claim 1, in an amount sufficient to exhibit activity against p-388 leukemia in said mouse and a pharmacologically acceptable adjuvant.

3. The compound according to claim 1, wherein $X_2$ is a nitro group, and Y is a hydrogen atom, a halogen atom or a trifluoromethyl group.

4. The compound according to claim 1, wherein $X_1$ is a hydrogen atom, and $X_2$ is a nitro group.

5. A method for treating p-388 leukemia in a mouse, which comprises administering the said mouse an N-benzoyl-N'-pyridazinyloxyphenyl urea compound as defined in claim 1, in an amount sufficient to exhibit activity against p-388 leukemia in said mouse.

6. The compound according to claim 1, wherein $X_1$ is a hydrogen atom, $X_2$ is a nitro group, Y is a halogen atom or a methyl group which may be substituted by fluorine, and Z is a halogen atom.

7. A method for treating p-388 leukemia in a mouse, which comprises administering to said mouse an effective amount of the composition of claim 2.

8. The compound according to claim 1, which is N-(2-nitrobenzoyl)-N'-[4-(6-bromo-3-pyridazinyloxy)-3-chlorophenyl]urea.

9. The compound according to claim 1, which is N-(2-nitrobenzoyl)-N'-[3-chloro-4-(6-chloro-3-pyridazinyloxy)phenyl]urea.

10. The compound according to claim 1, which is N-(2-nitrobenzoyl)-N'-[4-(6-bromo-3-pyridazinyloxy)-3-fluorophenyl]urea.

11. The compound according to claim 1, which is N-(2-nitrobenzoyl)-N'-[4-(6-chloro-3-pyridazinyloxy)-3-trifluoromethylphenyl]urea.

12. The compound according to claim 1, which is N-(2-nitrobenzoyl)-N'-[4-(6-chloro-3-pyridazinyloxy)-3-methylphenyl]urea.

* * * * *